(12) United States Patent
Von Schuckmann et al.

(10) Patent No.: US 8,474,447 B2
(45) Date of Patent: Jul. 2, 2013

(54) INHALER DEVICE

(75) Inventors: Alfred Von Schuckmann, Kevelaer (DE); Dieter Hochrainer, Schmallenberg (DE); Hubert Hoelz, Oberheimbach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 384 days.

(21) Appl. No.: 12/677,555

(22) PCT Filed: Aug. 28, 2008

(86) PCT No.: PCT/EP2008/061337
§ 371 (c)(1),
(2), (4) Date: May 5, 2010

(87) PCT Pub. No.: WO2009/037085
PCT Pub. Date: Mar. 26, 2009

(65) Prior Publication Data
US 2010/0229857 A1 Sep. 16, 2010

(30) Foreign Application Priority Data
Sep. 22, 2007 (DE) .......................... 10 2007 045 438

(51) Int. Cl.
*A61M 11/00* (2006.01)
*A62B 7/00* (2006.01)
*A62B 9/00* (2006.01)

(52) U.S. Cl.
USPC ............. 128/200.23; 128/200.14; 128/205.23

(58) Field of Classification Search
USPC ............. 128/200.14, 200.23, 200.24, 203.12, 128/203.15, 203.16, 203.21, 203.23, 205.23; 222/23, 30, 36; 604/58, 97.03
See application file for complete search history.

(56) References Cited

U.S. PATENT DOCUMENTS

| | | | |
|---|---|---|---|
| 7,195,134 B2 * | 3/2007 | Ouyang et al. | 222/36 |
| 7,407,066 B2 * | 8/2008 | Ouyang et al. | 222/36 |
| 7,448,342 B2 | 11/2008 | Von Schuckmann | |

(Continued)

FOREIGN PATENT DOCUMENTS

| | | |
|---|---|---|
| WO | 03107269 A1 | 12/2003 |
| WO | 2005020138 A1 | 3/2005 |
| WO | 2006051073 A1 | 5/2006 |

OTHER PUBLICATIONS

International Search Report PCT/EP2008/061337 mailed Dec. 19, 2008.

*Primary Examiner* — Justine Yu
*Assistant Examiner* — Valerie L Skorupa
(74) *Attorney, Agent, or Firm* — Michael P. Morris; David L. Kershner

(57) ABSTRACT

The invention relates to a hand-held device (1), as depicted in exemplary FIG. 4, for metered dispensing of sprayable substances, particularly medicaments for inhalation, with a cartridge (3) that can be moved into the dispensing position, by pressure being applied to a housing, and with a step-by-step indexing mechanism (11) which is entrained by the cartridge (3) in the opening travel thereof and which is used to record and display the dispensing actuations that have been performed. In order to suitably design a hand-held device of the type in question with a simplified structure, in such a way that the indexing steps can be performed smoothly and safely without connection to the cartridge, it is proposed that slits (19) extend obliquely only over part of the travel of the step-by-step indexing mechanism housing (34) and that the guide pins (33) guided therein move, over the remainder of the travel of the step-by-step indexing mechanism (11), parallel to the longitudinal axis (x-x) of the step-by-step indexing mechanism.

7 Claims, 9 Drawing Sheets

U.S. PATENT DOCUMENTS

| | | |
|---|---|---|
| 7,510,100 B2 | 3/2009 | Stradella et al. |
| 2005/0017020 A1* | 1/2005 | Eckert .............................. 222/30 |
| 2005/0209558 A1* | 9/2005 | Marx .......................... 604/97.03 |
| 2006/0163276 A1* | 7/2006 | Wong et al. ..................... 222/36 |

* cited by examiner

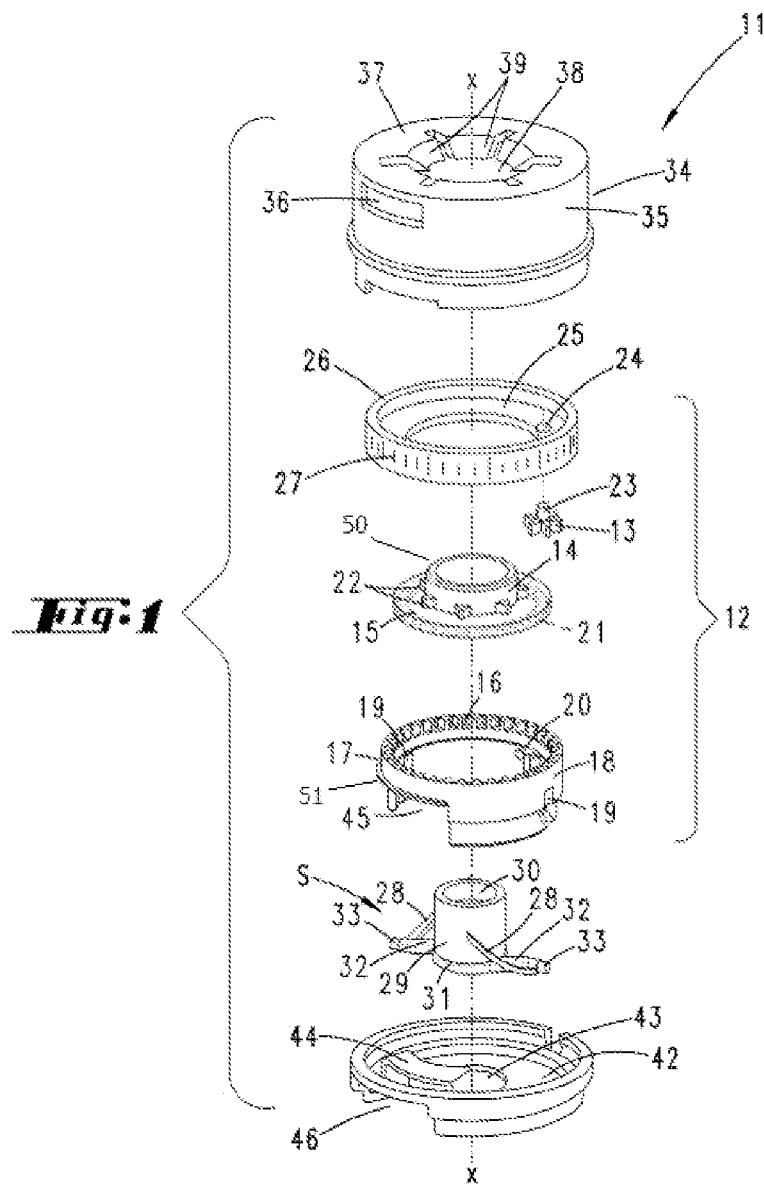

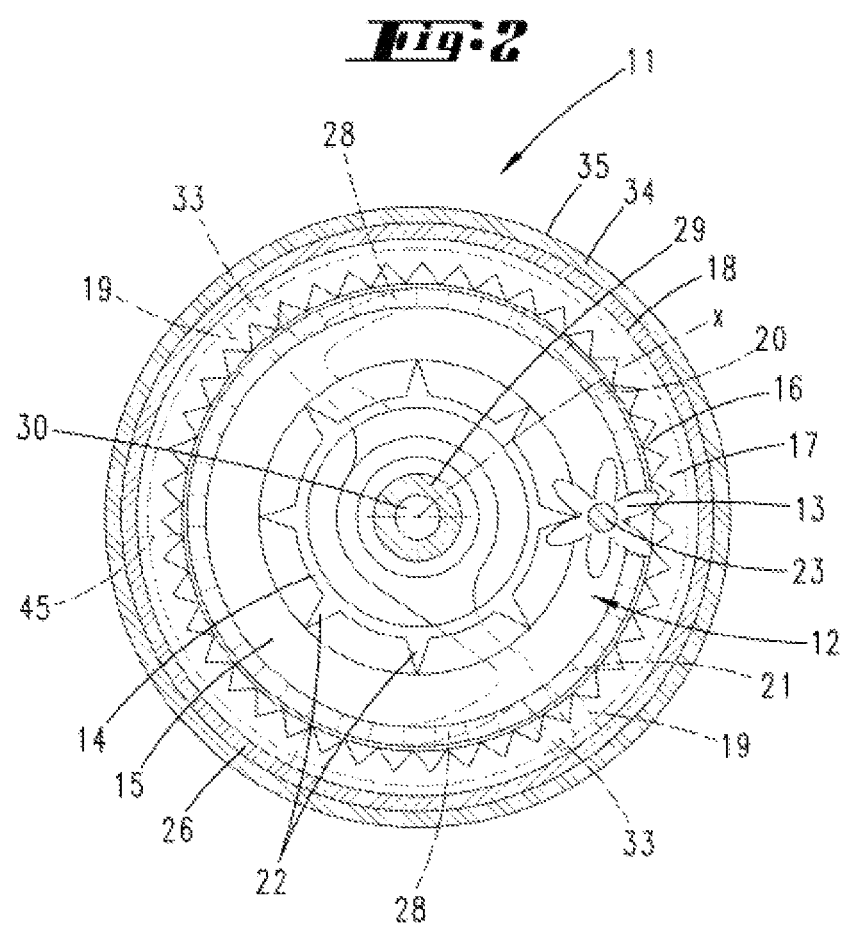

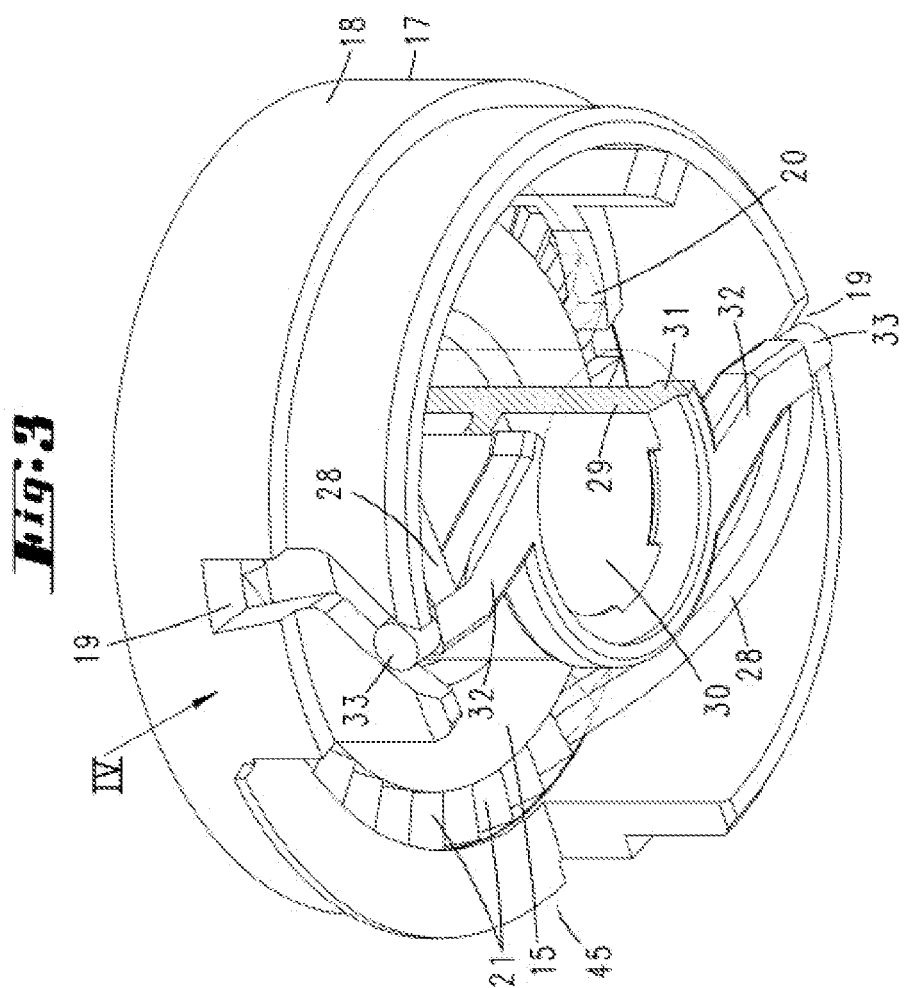

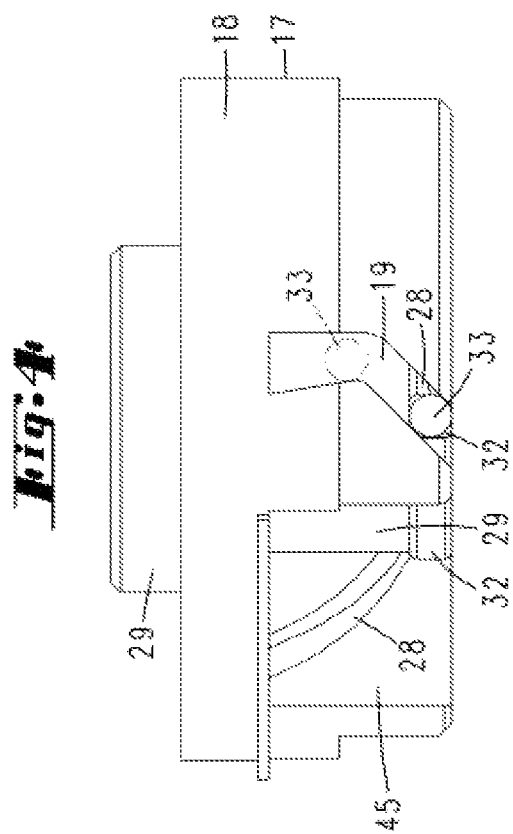

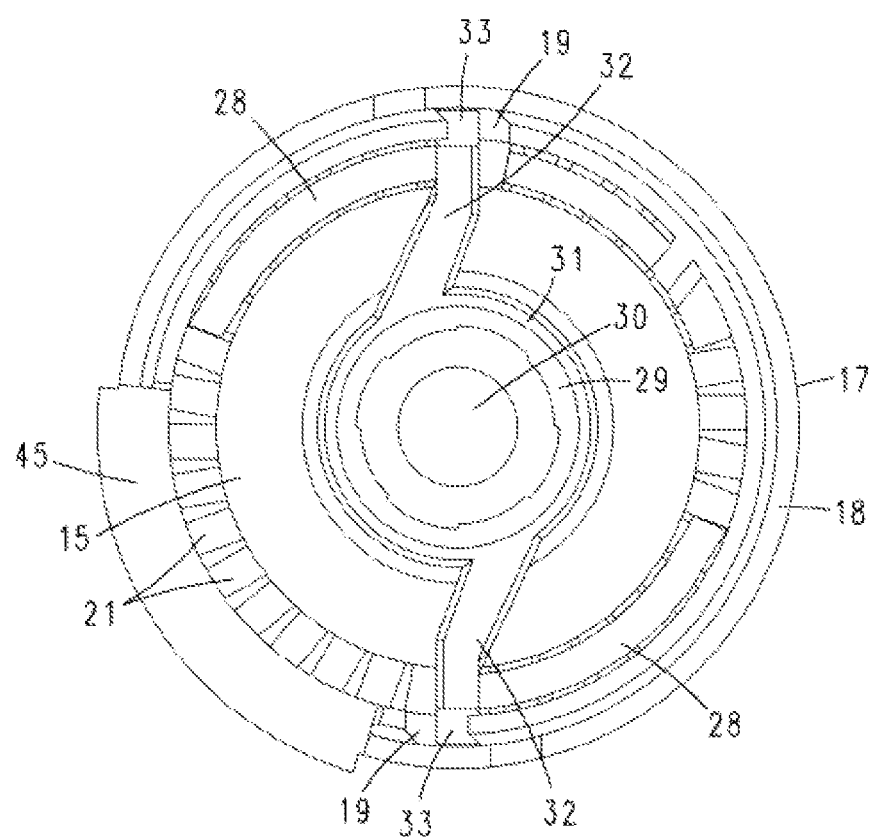

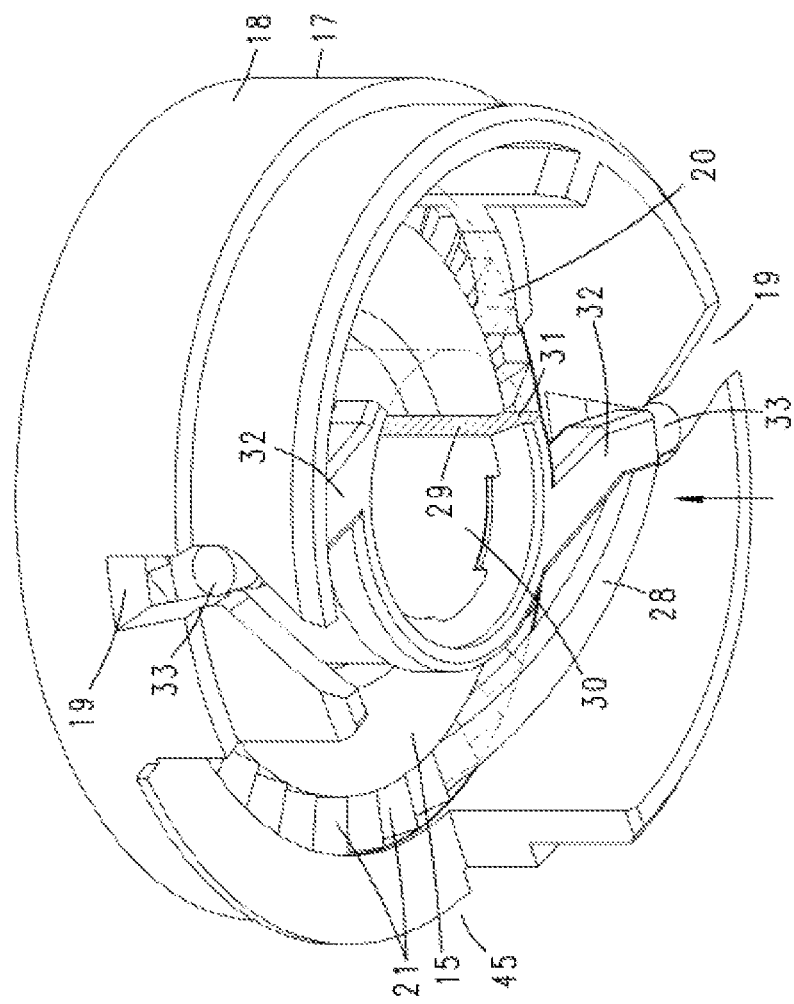

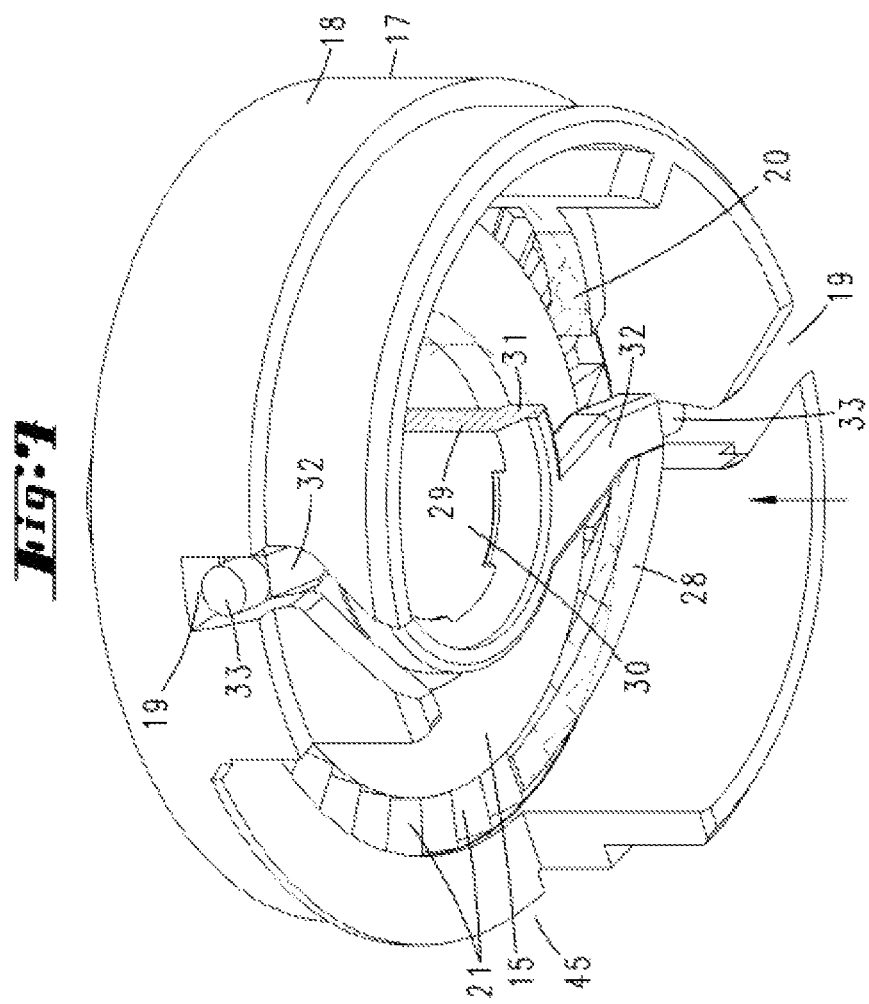

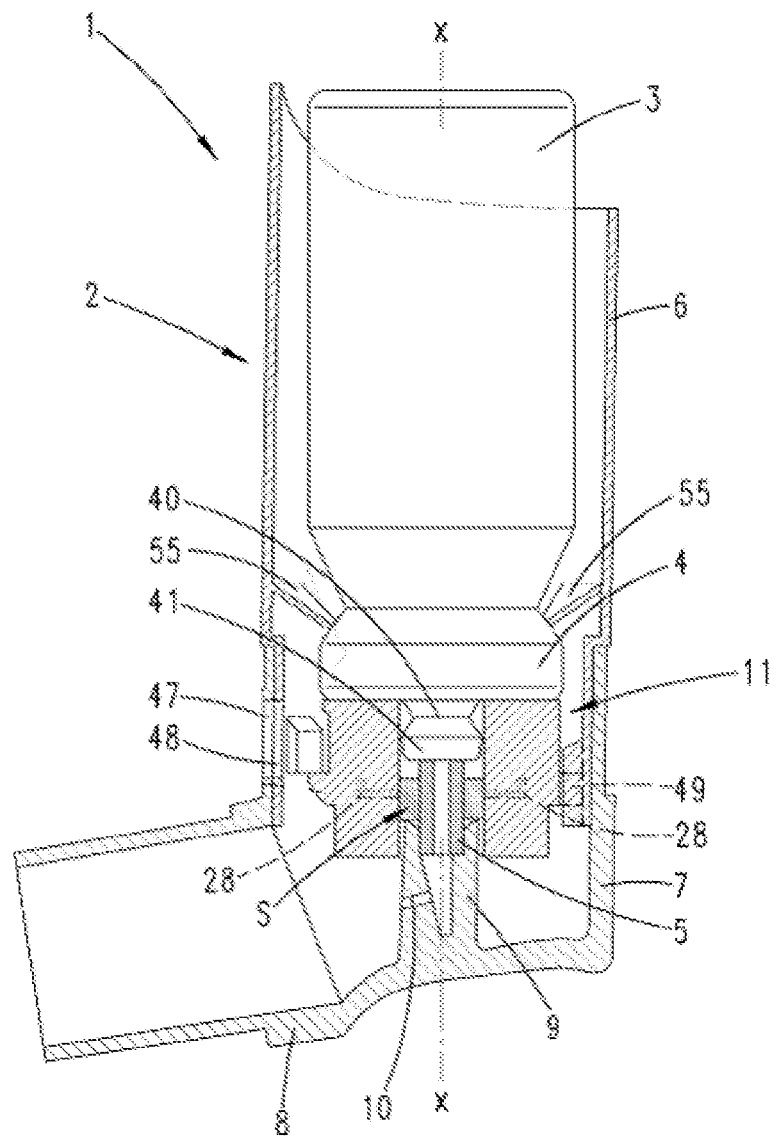

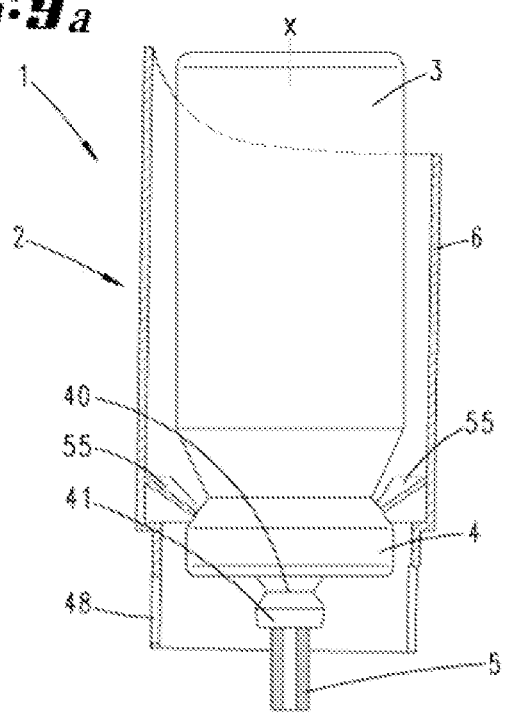
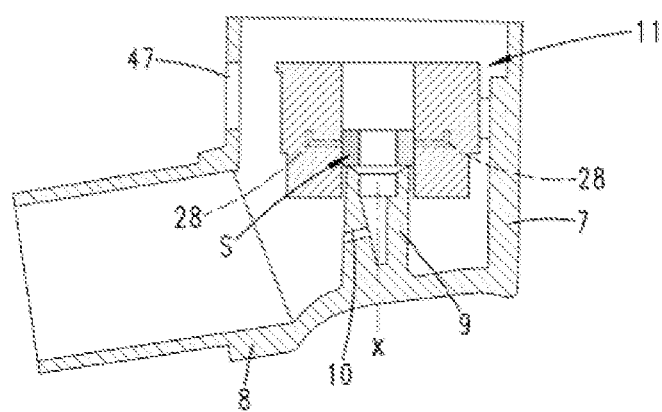

INHALER DEVICE

The invention relates to a hand-held device for metered dispensing of sprayable substances, particularly medicaments for inhalation, according to the preamble of the main claim.

Hand-held devices of the type in question are already known (WO 2006/051073). They are used in particular in medical aerosol therapy for treating diseases of the respiratory tract. The pressurised cartridge held in the housing contains the medicament that is to be inhaled, while in order to release or expel the medicament it is necessary to push the cartridge axially in the housing. The known solutions are complex and not very user-friendly, particularly in view of the internal tolerances of the step-by-step indexing mechanism and the fact that many patients have an unsteady hand.

The aim of the invention is therefore to provide a favourable construction of a hand-held device of the type in question with a simplified design so that in particular the indexing steps can be carried out easily and safely.

This problem is solved by the subject-matter of claim 1. A hand-held device of the type in question is created, which has considerable advantages, thanks to the chosen construction which does not take up much space for the indexing mechanism and also with regard to the maximum possible freedom from tolerances and guaranteed accurate counting. On actuation, the guide pins of the indexing pawl not only pass through the diagonal slot that is responsible for the rotation of the star-shaped arrangement of indexing pawls, but thereafter also pass through an axially extending slot portion which, besides lowering the graduated collar in front of the inspection window, develops a supplementary spring force of the indexing pawls, to ensure resetting of the step-by-step indexing mechanism as a whole, independently of the return stroke of the cartridge, which results from the resilience of the valve tube, in known manner. The step-by-step indexing pawls engage in the teeth of the sunwheel which is set in rotation thereby and preferably so does the latching pawl that prevents reverse rotation. The components interact in a manner which is as free from tolerances as possible.

The subject-matter of the invention will hereinafter be explained in more detail by reference to the attached drawings that show an embodiment by way of example. In the drawings:

FIG. 1 is a perspective exploded view of the step-by-step indexing mechanism for the hand-held device according to the invention;

FIG. 2 is a cross-section through the step-by-step indexing mechanism;

FIG. 3 is a schematic representation of the rotary drive area of the step-by-step indexing mechanism;

FIG. 4 is a side view thereof;

FIG. 5 is a bottom view thereof;

FIG. 6 is a representation as in FIG. 3 but with the housing partly shifted;

FIG. 7 is a representation as in FIG. 6 with the housing shifted further;

FIG. 8 schematically shows the hand-held device with the step-by-step indexing mechanism in the unactuated position;

FIGS. 9a and 9b together represent one possible removal method.

The hand-held device 1 shown in a schematic sectional view in FIG. 1 is used for the metered dispensing of sprayable substances, particularly medicaments for inhalation.

For this purpose the hand-held device 1 comprises first of all a hand-held device housing 2 into which a cartridge 3 containing the sprayable substance can be inserted. This cartridge 3 is axially movable in the housing 2.

In the usual way, the cartridge head 4 comprises a central valve tube 5 extending coaxially with respect to the cartridge 3. Medicament is dispensed through this valve tube 5 by an axial relative movement between the cartridge 3 and the housing 2.

The housing 2 is in two parts and essentially consists of two ring portions 6 and 7 arranged one above the other, the upper ring portion 6 being of shaft-like construction and the lower ring portion 7 comprising a mouthpiece 8 that is aligned substantially at right-angles to the direction of the shaft. The mouthpiece 8 can be closed off by means of a covering cap (not shown).

The valve tube 5 of the cartridge 3 is supported in an associated tubular support section 9 within the lower ring portion 7, while the cartridge 3 remains axially movable within the shaft-like ring portion 6 that surrounds the cartridge 3.

The support section 9 that clamps the valve tube 5 of the cartridge 3 in position and is formed within the lower ring portion 7 of the housing is provided with a flow channel 10 of reduced diameter relative to a portion that accommodates the end of the valve tube, this flow channel being fluidically connected to the valve tube 5, while the end of the flow channel 10 remote from the valve tube 5 faces towards the mouthpiece 8.

The two ring portions 6 and 7 are adapted to be fitted into one another in the embodiment shown by way of example. Alternatively, the two parts may also be joined together by means of a screw thread, e.g. a coarse thread with a high pitch.

The arrangement of the cartridge 3 in the housing 2 is such that the cartridge head 4 is placed in the housing 2 substantially level with the connecting region between the ring portion 6 and ring portion 7.

Centrally underneath the end wall of the cartridge 3 on the opening side is arranged a step-by-step indexing mechanism 11, overlapping with the valve tube 5 of the cartridge. This mechanism 11 is used to register and indicate the number of dispensing operations that have been carried out, depending on the number of opening strokes of the cartridge 3 that have occurred.

The step-by-step indexing mechanism 11 is shown in FIG. 1 in an exploded perspective view. The central component of the step-by-step indexing mechanism 11 is an epicyclic gear 12, consisting of a planet wheel 13, a sunwheel 14 which rests on a disc 15 that has teeth on its underside and a gear rim 16 that cooperates with the planet wheel 13. This gear rim 16 is formed on the inside of the wall of a non-rotatably secured ring 17 in the shape of a tube section. The outer wall 18 of the ring 17 is pierced, in diametrically opposite areas, by slots 19 proceeding diagonally upwards in the indexing direction, which open downwards towards the edge of the ring remote from the gear rim 16. The ring 17 further comprises an edge 51 which supports the housing 34 of the step-by-step indexing mechanism.

The gear rim 16 extends axially over approximately half the height of the ring 17, the outer wall 18 of which is constructed to taper radially in graduated manner towards the end edge of the ring remote from the gear rim 16.

Underneath the disc 15, inside the outer wall 18 of the ring 17, is formed a latching pawl 20. This is offset radially inwards from the gear rim 16 in relation to an outline of the ring; it engages correspondingly in a circular space drawn radially inwards towards the gear rim 16. Moreover, the arrangement of the latching pawl 20 that is constructed to be resilient substantially in the vertical direction is such that the pawl engages in the teeth 21 from below.

The diameter of the disc 15 bearing the sunwheel 14 is chosen to be slightly smaller than the internal diameter of the ring 17 in the region of the gear rim 16. The sunwheel 14 and disc 15 are preferably made in one piece, from the same material.

The teeth 21 provided on the underside of the disc 15 run around its edge and are in the form of saw teeth 21.

The sunwheel 14 has coarse teeth. Thus, in the embodiment shown, eight sunwheel teeth 22 are uniformly distributed over the circumference of the sunwheel 14. These teeth 22 cooperate during the rotation of the sunwheel with the planet wheel 13 that is arranged in the same plane between the sunwheel 14 and the gear rim 16 of the ring 17.

The planet wheel 13 has an axial pin 23 that projects upwards on one side, i.e. away from the disc 15 of the sunwheel 14. This pin 23 is rotatably held in a bore 24 in the region of a flange 25 of a graduated collar 26 facing radially inwards in the manner of a washer. The graduated collar 26 is provided on the outer wall with scale gradations 27 running round it, the scale gradations corresponding in each case to a number of individual rotary steps of the planet wheel 13 that drives the graduated collar 26.

The stepwise displacement of the sunwheel 14 or of the disc 15 fixedly connected thereto is carried out via step-by-step indexing pawls 28 that are designed to give way in a substantially vertical resilient manner. They pass through the underside to engage in the saw teeth 21 of the disc 15.

The step-by-step indexing pawls 28 are arranged diametrically opposite in relation to the main axis x of the step-by-step indexing mechanism 11 as a whole. For this purpose, first a cylindrical central body is provided in the form of a hub 29 with a central axial through-bore 30. It diameter is slightly larger than the external diameter of the cartridge valve tube 5 that is to be passed through this through-bore 30. A tubal bearing 50 extends axially toward the housing 34 and above a sunwheel 14 which rests on the disk 15.

At its base, the hub 29 merges into a radially widened collar 31. Guide portions 32 projecting diametrically opposite one another in the radial direction are formed on this collar 31, these guide portions 32 each forming, in the region of their free ends, a guide pin 33 that lies in the associated slot 19 of the ring 17.

The step-by-step indexing pawls 28 are each rooted with a horizontal portion on the guide portions 32 leaving the guide pins 33 projecting radially outwards over the horizontal portion. The step-by-step indexing pawls 28 projecting from the horizontal portions are directed diagonally outwards, possibly enclosing an angle of 45 degrees with the horizontal, matched to the inclination of the slots 19 in the ring 17. The star arrangement of step-by-step indexing pawls thus formed has the reference numeral S.

The star-shaped indexing pawl arrangement S, the ring 17 comprising the inner gear rim 16, the disc 15 formed in one piece with the sunwheel 14 and the graduated collar 26 are aligned concentrically with one another on the axis x, the height of the ring 17 being chosen such that both the star arrangement S and the sunwheel 14 together with the disc 15 are accommodated therein.

The slots 19 are made up of two sections, one of which is directed diagonally with respect to the longitudinal axis x-x and forces the rotation of the step-by-step indexing pawls, while the second section, adjoining it, is directed parallel to the longitudinal axis x-x. The latter widens out to some extent towards the upper end, so that the guide pins 33 enter it with play (cf. FIG. 7), particularly counter to the direction of rotation forced by the first diagonally extending portion of the slot 19. The travel which is allowed by the star-shaped indexing pawl arrangement in the linearly upwardly directed slot portion causes further tensioning of the inner spring ring of the step-by-step indexing pawls 28—without any rotation thereof—thus substantially increasing the force—after the cartridge has been released—for restoring the step-by-step indexing mechanism to the starting position.

The entire epicyclic gear 12 and the star-shaped indexing pawl arrangement S and the graduated collar 26 are accommodated in a pot-like housing 34 for the step-by-step indexing mechanism, with an outer diameter that is matched to the outer diameter of the cartridge 3.

The housing 34 has an outer wall 35. This comprises an inspection window 36 through which the scale gradations 27 of the graduated collar 26 can be seen.

The top 37 of the housing has a central aperture 38 which, in the embodiment shown in FIG. 1, is surrounded by latching spring tongues converging conically towards the inside of the housing in the embodiment 39 shown in FIG. 1. The diameter of the aperture is matched to a diameter of a waist section 40 of a collar 41 projecting centrally over the end wall of the cartridge 3 on the opening side, out of which collar 41 the valve tube 5 extends.

The base 42 of the housing is formed by a separate part. The latter is connected to the housing 34 to accommodate the individual parts of the step-by-step indexing mechanism as described hereinbefore, thus for example welded thereto or attached thereto by force-fitting.

The plate-shaped housing base 42 has a central bore for the valve tube 5 to pass through. In addition, a latching member 44 is formed on the housing base 42, serving to trap the ring 17 in the correct orientation in a window-like recess 45 formed accordingly in the outer wall 18 thereof.

In the same angle region in which the fitting member 44 is arranged on the base, the outer wall of the housing base 42 has a free cut-out 46. This is associated, in the installed position, with the region of the outlet cross-section of the flow channel 10 in the lower ring portion housing 7.

The step-by-step indexing mechanism 11 operates as follows:

The indexing members (star-shaped indexing pawl arrangement S, ring 17, disc 15, planet wheel 13 and graduated collar 26) and also the housing 34 with the housing base 42 are arranged on axes that extend in the longitudinal direction x-x of the cartridge. Thus, with the exception of the planet wheel 13, all the other components of the step-by-step indexing mechanism 11 are located on the longitudinal axis x-x of the cartridge. The step-by-step indexing mechanism 11 is arranged correspondingly concentrically with respect to the valve tube 5 in the shadow of the cartridge 3 inside the housing 2, specifically in the space left between the head 4 of the cartridge and the support section 9 of the housing 2. The step-by-step indexing mechanism 11 is supported with the hub 29 of the star-shaped indexing pawl arrangement S, that is mounted centrally in the step-by-step indexing mechanism housing 34, on the end face of the support section 9 of the inhaler housing 2. The central axis x of the step-by-step indexing mechanism 11 is taken over by the axis of the body of the cartridge 3. The valve tube 5 passing through the hub 29 provides additional centring of the entire step-by-step indexing mechanism unit.

When an actuating stroke of the cartridge 3 is carried out and hence the latter is shifted vertically in the direction of the support section 9 the indexing mechanism housing 34 is advanced over the head 4 of the cartridge, with relative movement of the housing 34, the planet wheel gear 12 and the graduated collar 26 to the star-shaped indexing pawl arrangement S, which comes to bear on the support section 9.

As a result, the tensioning step-by-step indexing pawls 28, by virtue of the rotary sliding of the star-shaped indexing pawl arrangement S in the diagonal portions of the slots 19 in the ring 17 on the outer wall side, cause the saw-toothed disc 15 to advance rotationally step by step. In correlated manner, the sunwheel 14 rotates by the same angular amount. The step-by-step indexing pawls 28 move out of the diagonal alignment towards a plane that is aligned perpendicularly with the longitudinal axis x-x.

Owing to the fact that the sunwheel 14 has only eight teeth uniformly distributed over the circumference, not every stepwise rotary movement of the sunwheel 14 necessarily leads to a rotary movement of the planet wheel 13. Rather, the rotation of the planet wheel 13 about its axis and an associated rotary movement of the graduated collar 26 only take place after a number of individual rotary steps of the sunwheel 14 have occurred. Then, further displacement of the cartridge 3 requires the guide pins 33 to move in the portions of the slot 19 that extend in the longitudinal direction x-x, which causes a further increase in the restoring force stored in the pawls 28, without any additional rotation of the star-shaped indexing pawl arrangement.

Associated with the inspection window 36 on the housing side, the associated portions of the housing ring portions 6 and 7 also have inspection windows 47, 48 which, thanks to their chosen position facing the mouthpiece 8 of the housing 2, are within the field of vision of the user of the hand-held device 1. For correctly oriented insertion of the step-by-step indexing mechanism 11, the latter is provided with a guide fin 49 projecting radially from the housing 34, which engages in a vertical groove (not shown in detail) inside the housing 2 that permits a sliding movement during the actuating stroke.

A latching action between the step-by-step indexing mechanism 11 and cartridge 3 in the region of the collar 41 on the cartridge head side may also be chosen such that when the cartridge 3 is removed from the housing 2 the step-by-step indexing mechanism 11 is also pulled out, remaining on the cartridge 3. However, as shown in FIG. 9, for example, the cartridge and the indexing mechanism may be separately removable, particularly as the step-by-step indexing mechanism is self-sufficient in terms of springing back.

All the features disclosed are (per se) essential to the invention. Hereby included in the disclosure of the application is the content of the associated/attached priority documents (copy of the earlier application) for the purpose of incorporating features of these documents in claims of the present application.

The invention claimed is:

1. Hand-held device (1) for metered dispensing of sprayable substances that are medicaments for inhalation, having a cartridge (3) that during an opening stroke is movable into a dispensing position in a housing (2) by pressing and a step-by-step indexing mechanism (11) that is also moved by the cartridge (3) during the opening stroke of said cartridge (3), for registering and displaying the number of dispensing actuations carried out, said step-by-step indexing mechanism (11) having a graduated collar (26) arranged circumferentially, concentrically with respect to a valve tube (5), in front of an inspection window (36, 47, 48) and a disc (15) with teeth on its underside into which two step-by-step indexing pawls (28) engage as a housing (34) of the step-by-step indexing mechanism is axially moved, which is forced into a rotary movement by guide pins (33) movable in diagonal slots (19), characterised in that the diagonal path of the slots (19) extends over only part of the stroke height of the step-by-step indexing mechanism housing (34) and the guide pins (33) move over the remaining travel of the step-by-step indexing mechanism (11) parallel to the longitudinal axis (x-x) of the step-by-step indexing mechanism, wherein the disc (15) further comprises a tubal bearing (50) that extends axially toward the housing (34) and above a sunwheel (14) which rests on disk (15).

2. Hand-held device according to claim 1, characterised in that the guide pins are guided in the slots with play over the remainder of the stroke.

3. Hand-hold device according to claim 1, characterised in that there are two step-by-step indexing pawls (28) and in that the step-by-step indexing mechanism comprises a latching pawl (20) which engages in the region between the two step-by-step indexing pawls (28) in the same teeth (21) as the step-by-step indexing pawls (28).

4. Hand-held device according to claim 1, characterised in that a spring tension that opposes the opening stroke is contained within the step-by-step indexing pawls.

5. Hand-held device according to claim 1, characterised in that the step-by-step indexing mechanism housing (34) is guided in linear manner in the housing (2).

6. Hand-held device according to claim 5, characterised in that the guiding is achieved by means of a guide fin (49) in a vertical groove.

7. Hand-held device according to claim 1, characterised in that the slots (19) are formed in a non-rotatably secured ring (17) in the shape of a tube section, the ring (17) comprising an edge (51) which supports the housing (34) of the step-by-step indexing mechanism.

* * * * *

UNITED STATES PATENT AND TRADEMARK OFFICE
CERTIFICATE OF CORRECTION

PATENT NO. : 8,474,447 B2  Page 1 of 1
APPLICATION NO. : 12/677555
DATED : July 2, 2013
INVENTOR(S) : Von Schuckmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 507 days.

Signed and Sealed this
Eighth Day of September, 2015

Michelle K. Lee
*Director of the United States Patent and Trademark Office*